(12) United States Patent
Lowe

(10) Patent No.: US 7,036,687 B1
(45) Date of Patent: May 2, 2006

(54) LIQUID BEVERAGE MIXING CHAMBER

(75) Inventor: Kevin G. Lowe, Virden, IL (US)

(73) Assignee: Bunn-O-Matic Corporation, Springfield, IL (US)

( * ) Notice: Subject to any disclaimer, the term of this patent is extended or adjusted under 35 U.S.C. 154(b) by 352 days.

(21) Appl. No.: 10/641,202

(22) Filed: Aug. 13, 2003

Related U.S. Application Data

(60) Provisional application No. 60/403,194, filed on Aug. 13, 2002, provisional application No. 60/403,081, filed on Aug. 13, 2002.

(51) Int. Cl.
B67D 5/60 (2006.01)

(52) U.S. Cl. .............................. 222/145.5; 222/145.6; 222/129.1; 222/459

(58) Field of Classification Search ..... 222/129–129.4, 222/145.5, 459, 145.6, 145.7, 64, 145.8, 222/54, 161–163, 145.1, 52; 99/323.2, 323.3; 366/165.3, 165.1, 165.2
See application file for complete search history.

(56) References Cited

U.S. PATENT DOCUMENTS

| 3,919,975 | A | * | 11/1975 | Duncan | 119/14.05 |
| 4,193,522 | A | | 3/1980 | Edelbach | |
| 4,291,575 | A | * | 9/1981 | Frissora | 73/302 |
| 4,544,084 | A | * | 10/1985 | Cleland | 222/56 |
| 4,753,370 | A | * | 6/1988 | Rudick | 222/105 |
| 5,000,352 | A | * | 3/1991 | Cleland | 222/129.2 |
| 5,303,846 | A | * | 4/1994 | Shannon | 222/54 |
| 5,316,180 | A | * | 5/1994 | Cleland | 222/56 |
| 5,375,739 | A | * | 12/1994 | Granfelt | 222/56 |
| 5,797,313 | A | * | 8/1998 | Rothley | 99/483 |
| 6,202,894 | B1 | | 3/2001 | Struminski et al. | |
| 6,387,424 | B1 | * | 5/2002 | Funk | 426/231 |
| 6,419,120 | B1 | * | 7/2002 | Bertone | 222/129.4 |
| 6,644,620 | B1 | | 11/2003 | Johnson et al. | |
| 6,871,761 | B1 | * | 3/2005 | Fox | 222/129.1 |

* cited by examiner

Primary Examiner—Frederick C. Nicolas
(74) Attorney, Agent, or Firm—Barnes & Thornburg LLP

(57) ABSTRACT

The present disclosure relates to a system method and apparatus for mixing a beverage produced from a concentrate. The apparatus includes a mixing chamber having a removable cover with at least one protrusion formed thereon for disrupting a flow of beverage into the mixing chamber. Additionally, an area of reduced size within the mixing chamber may be provided which causes a beverage entering the mixing chamber to pool therein.

33 Claims, 3 Drawing Sheets

LIQUID BEVERAGE MIXING CHAMBER

This application claims the benefit of U.S. Provisional Application No. 60/403,194 filed Aug. 13, 2002 and U.S. Provisional Application No. 60/403,081 filed Aug. 13, 2002.

BACKGROUND

The present disclosure contemplates a method, system and apparatus for producing and dispensing food products such as beverages made from a concentrate.

There are numerous beverage preparation systems that use a concentrate substance to prepare a beverage. Typically, the beverage concentrate is diluted with another substance, such as water, to prepare the desired resultant beverage, for example coffee, tea or juice to name a few. The concentrate may be in the form of a frozen, chilled, room temperature or heated prepackaged liquid or may also be a freshly brewed or otherwise prepared concentrate liquid. Additionally, powdered, gel, gaseous, granulated or other concentrates may be used.

The concentrate may be contained in a variety of containers. For example, one form of packaged beverage concentrates come in a "bag-in-box" arrangement where a plastic bag containing the beverage concentrate is contained within a box. Other containers such as metallic cylinders or plastic bottles may be used. The "bag-in-box" containing the desired concentrate is attached to a dispensing apparatus. Heated water in the case of coffee or tea, or chilled or room temperature water in the case of juice is then combined with a predetermined volume of concentrate to yield a resulting beverage with desired flavor characteristics. The proper volume of diluting water and concentrate are typically measured as a factor of time. For example, for a unit of beverage to be produced, a pump dispensing a concentrate must operate for a preselected period of time to deliver a predetermined volume of concentrate. At the same time, a valve must be opened for a preselected period of time to deliver a predetermined volume of diluting water. The combination of the pump and valve operating for preselected periods of time will produce a beverage with a desired flavor characteristic.

The concentrate and diluting water may be alternatively introduced at separate times into a container from which the resulting beverage is dispensed or consumed. Another possibility is to combine the concentrate and diluting water in a mixing chamber prior to dispensing into a container.

The concentrate and diluting water must mix thoroughly in order for a resulting beverage to be enjoyed at an optimum level. Mixing has been accomplished by combining concentrate and diluting water prior to dispensing of a beverage through the use of agitators, mechanical devices and physical shapes of serving spouts. Mixing has also been accomplished by separately dispensing a concentrate and a diluting water directly into a container.

It is expected that there are other beverage dispensing and diluting systems which will benefit from the present disclosure which provides improved accuracy, consistency, repeatability and uniformity in the mixing and dispensing of beverages formed from a concentrate.

The present disclosure relates to a method, system and apparatus for producing and dispensing beverages made from a concentrate. The present disclosure includes a mixing chamber which allows a conductivity detecting system to more accurately monitor the conductivity of a diluted beverage during the mixing and dispensing process, thereby producing a more uniform beverage.

The present disclosure includes a mixing chamber and a method of introducing concentrate and diluting water into the mixing chamber which will give rise to more accurate detection of conductivity of the resulting beverage within the mixing chamber. Further, the mixing chamber will yield a more uniform beverage in both taste and appearance.

Briefly, a method, system and apparatus for producing and dispensing beverages made from a concentrate is disclosed. A conductivity detecting system is provided within a mixing chamber for measuring the conductivity of a beverage contained therein. The mixing chamber is a component of a mixing system. The mixing system contemplates a concentrate supply line and a vent line located proximate to an outlet end of an angled inlet tube carrying diluting water into a mixing chamber. The mixing chamber includes a structure with a removable portion, such as a cover having protrusions for homogenizing or mixing the concentrate and the diluting water as they enter the mixing chamber. Homogenizing is meant to describe the process of combining a concentrate and a diluting water into a beverage having uniform consistency. Further, a reduced diameter restriction in the mixing chamber is provided to allow for pooling of the resulting homogenized beverage which allows for further mixing as well as measurement by conductivity probes proximate to the area of restricted diameter.

Additional features will become apparent to those skilled in the art upon consideration of the following detailed description of drawings illustrating at least one embodiment of the disclosure.

BRIEF DESCRIPTION OF THE DRAWINGS

The detailed description particularly refers to the accompanying figures in which.

DETAILED DESCRIPTION

Figure 1:
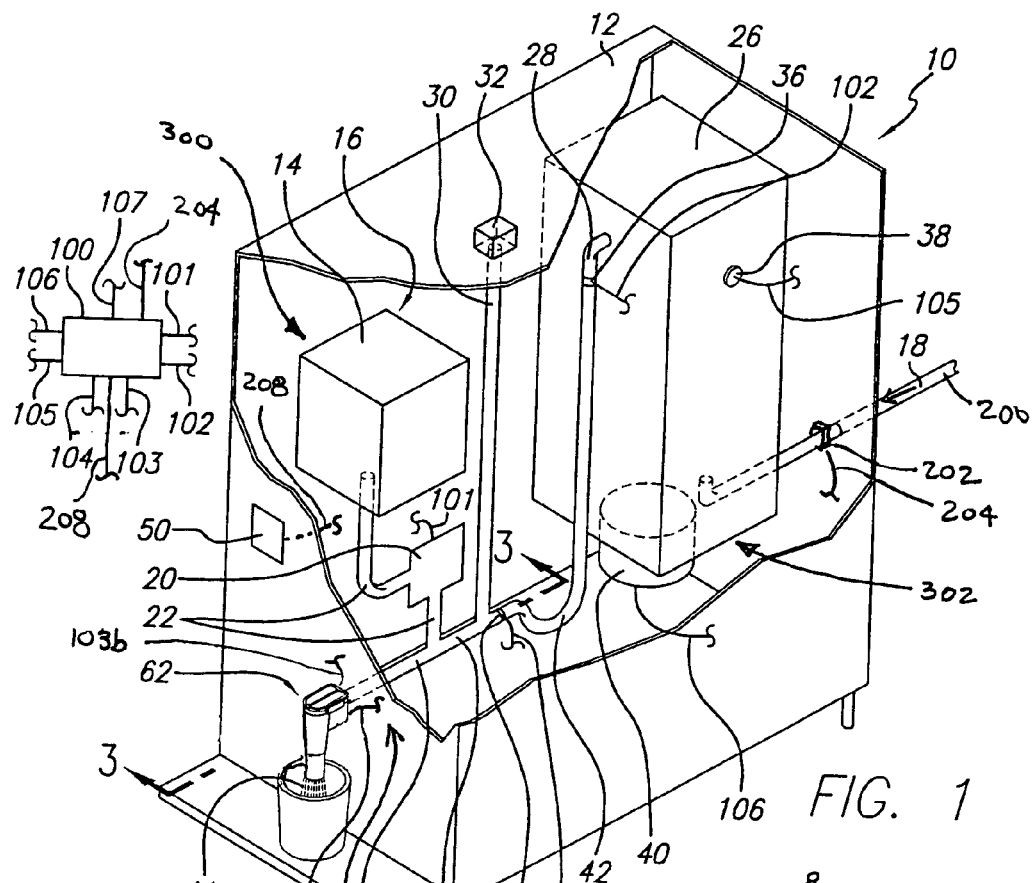
FIG. 1 is a diagrammatic perspective view of a beverage dispensing system with a conductivity detecting system.

While the present invention may be susceptible various modifications and alternative forms, there is shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings. The intention of this disclosure is to cover all modifications, equivalents, and alternatives falling within the spirit and scope of the invention as defined by the appended claims.

U.S. Pat. No. 6,387,424 issued to Robert C. Funk on May 14, 2002 and assigned to the assignee of the present application is expressly incorporated herein by reference.

Terms including brewed, brewing, brewing substance, brewing liquid, beverage, and brewed beverage as used herein are intended to be broadly defined as including but not limited to the brewing of coffee, tea and any other brewed beverage. This broad interpretation is also intended to include, but is not limited to any process of infusing, steeping, reconstituting, diluting, dissolving, saturating or passing a liquid through or otherwise mixing or combining a beverage substance with a liquid such as water without a limitation to the temperature of such liquid unless specified. This broad interpretation is also intended to include, but is not limited to beverage substances such as ground coffee, tea, liquid beverage concentrate, powdered beverage concentrate, freeze dried coffee or other beverage concentrates, to obtain a desired beverage or other food.

With reference to the figures, a beverage dispensing system 10 is shown in FIG. 1. This system generally produces a beverage 11 by combining a beverage concentrate 14 with a diluting water 18. A housing 12 having a generally rectangular shape is diagramatically shown in FIG. 1. The housing 12 contains a number of components which form the beverage dispensing system 10. The housing 12 also makes the beverage dispensing system 10 more sanitary and user friendly by allowing a user access to only a serving spout assembly 62 and a control panel 50. It is contemplated that any number of geometric shapes may serve the same function as the rectangular shaped housing 12 shown in FIG. 1. With reference to the diagrammatic illustrations as shown in FIG. 1 it is intended that the present disclosure and invention set forth in the claims is not to be limited by these illustrations. Rather the illustrations are provided in a diagrammatic form so as to incorporate all variations on such diagrammatic forms.

Turning to the components of the beverage dispensing system 10, the beverage concentrate 14 is contained within a container 16. The beverage concentrate 14 may be a concentrated coffee, tea, juice or other beverage and may come in liquid, powder, gel, gaseous, granular, or other form. In one embodiment, the beverage concentrate 14 is a coffee concentrate contained in a "bag-in-box" container. It is contemplated that other suitable containers known to those of skill in the art may be used to provide a beverage concentrate 14. While a bag-in-box container is described, additional containers such as refillable and replaceable containers, other disposable containers or connections to other concentrate supplying devices which are known in the art could be employed. Additionally, a freshly brewed beverage concentrate 14 may be provided for use in the beverage dispensing system 10 of the present disclosure. A system for providing brewed beverage concentrate could be in the form such as the Omni Beverage System manufactured by Bunn-O-Matic Corporation, assignee of the present application, and marketed by Procter and Gamble Corporation of Cincinnati, Ohio. All information relating to the Omni Beverage System is incorporated herein by reference.

The container 16 is connected by a concentrate tube 22 to a pump 20 which is controlled by a controller 100 over a line 101. It is contemplated in an embodiment that the pump 20 is a variable speed pump. An example of a pump which might be employed in the present system is shown in U.S. Pat. No. 6,419,466 issued to Kevin Lowe and Robert Funk on Jul. 16, 2002 and assigned to the assignee of the present application, which patent is expressly incorporated herein by reference. In response to a signal from controller 100, pump 20 operates, causing a variable volume of beverage concentrate 14 to be introduced into an inlet tube 24 where the beverage concentrate 14 comes into contact with the diluting water 18. The components including the container 16, pump 20 and tube 22 with the pump 20 being connected to the controller 100 comprise one form of means for delivering concentrate 300 or a controllable concentrate dispensing assembly.

The use of the pump 20 in this system provides a controllable concentrate dispenser. It is envisioned that the pump and concentrate could be positioned external to the housing 12. Furthermore, the pump may take a variety of forms such as peristaltic pump, piston pump, pressurized cylinder pump as well as any other form of pump which might help deliver concentrate to the system. Additionally, it is envisioned that the concentrate 14 could be delivered by gravity through the concentrate tube 22. Instead of a pump 20 a controllable valve may be provided to controllably open and close to deliver a metered amount of concentrate from the concentrate source or container 16 to the system.

While a controller 100 is shown in FIG. 1 generally external to the housing it is envisioned that the controller 100 may be incorporated into the housing to provide a self contained system. In this regard, the lines indicated to be running or otherwise connecting components of the system to the controller 100 are shown in broken form in the interest of clarity. It will be understood by one of skill in the art that a controller of known construction can be provided to controllably operate a variety of components of the system to coordinate and synchronize operation of the system to achieve the desired methods and functions disclosed herein. A variety of forms of such controller 100 expect to be within the skill of one of ordinary skill in the art employing micro processing systems and circuits as well as memory systems and circuits. The memory components providing the ability to program and store desired functionality and control of the various components. The controller 100 has been shown external to the housing 12 in the interest of clarity.

In one embodiment, the diluting water 18 is heated in a reservoir 26 to a predetermined temperature. The temperature is regulated by a thermostat 38, which is coupled over a line 105 to controller 100. In response to signals from thermostat 38, a heating element 40 is activated and deactivated by controller 100 over a line 106 to maintain the diluting water 18 at a predetermined temperature. This embodiment would be useful in an application where hot beverages were desired, such as coffee, tea or hot chocolate. A variety of beverage dispensing systems which use a heated water system provided by Bunn-O-Matic Corporation, Springfield, Ill., all such systems being incorporated herein by reference. For example, such as the Bunn-O-Matic FMD powdered beverage producing systems provide an example of a dispensing system which incorporates concentrate and heated water in which the concentrate is reconstituted by mixing with heated water to produce a desired beverage.

With reference to FIG. 1, incoming water 18 is generally provided to the reservoir 26 through water line 200. Controllable inlet valve 202 is coupled to the controller over line 204. In response to a signal from controller 100, the inlet valve 202 is opened to admit water 18 through line 200. Generally, the water in line 200 is under normal line pressure and is introduced to the reservoir 26 under such line pressure.

Reservoir 26 is connected to an inlet tube 24 by a water tube 28. Diluting water 18 from the reservoir 26 is introduced into water tube 28 through a controllable valve 36. Controllable valve 36 is coupled to controller 100 over a line 102. In response to a signal from controller 100 over line 102, controllable valve 36 opens and causes diluting water 18 contained within reservoir 26 to fill water tube 28. Water will not flow from the reservoir 26 even when the inlet valve 202 is open until the valve 36 is open. Once the valve 36 is open, water will flow into the reservoir from line 200 under line pressure and will generally exit the reservoir 26 under approximately the same pressure. The incoming water 18 is introduced toward the bottom of the reservoir 26 so as to position the unheated water close to the heating device or element 40 for more rapid heating. Water in the upper portion of the reservoir 26 is generally at a higher temperature and therefore used during the reconstituting process.

The outflow of diluting water 18 from water tube 28 into inlet tube 24 is regulated by a controllable flow restrictor 44 of known construction. Flow restrictor 44 is coupled to controller 100 over a line 107. In response to signals from controller 100 over line 107, flow restrictor 44 may decrease or increase the flow of diluting water 18 into inlet tube 24. For example, a flow rate of 2.5 ounces per second may be achieved when the flow restrictor 44 fully open. This flow rate may then be reduced to 1.8 ounces per second when the flow restrictor 44 is restricting the fluid flow into inlet tube 24. Thus, controllable valve 36 and flow restrictor 44 work in cooperation with one another to regulate the flow of diluting water 18 in a downstream 25 direction towards concentrate tube 22.

Alternatively, the flow restrictor 44 can be provided in a non-controllable form such as a sleeve which is inserted into inlet tube 24. The internal diameter of inlet tube 24 being generally equal to the external diameter of the flow restrictor 44. The flow restrictor 44 in this configuration, has an inner diameter which is smaller than the internal diameter of the inlet tube 24, resulting in a restriction of the flow in the inlet tube 24.

The components and systems used to deliver dilution material, herein described as diluting water, comprise one form of means for delivering dilution material 302 or a controllable dilution material dispensing assembly. In the embodiment shown and described herein the means 302 include the reservoir 26, inlet line 200, valves 202, 36, lines 28, 42 and any other components to deliver water for mixing with the concentrate.

It is contemplated that other beverages 11 may be produced by beverage dispensing system 10 which require different temperature ranges for maximum enjoyment. For example, a variety of juices may be produced from a beverage concentrate 14. In such an application, diluting water 18 could be introduced into water tube 28 through controllable valve 36 and flow restrictor 44 either chilled or at ambient temperature. In this embodiment, the reservoir 26 may be used as a way of providing an accumulation reservoir for chilling or maintaining a quantity of ambient temperature water. Alternatively, the water may flow through a chilling coil without accumulation in a reservoir or may flow directly to the inlet tube 24 as in the form of an ambient temperature system. Similarly, the concentrate could be chilled or at ambient temperature.

Figure 3:
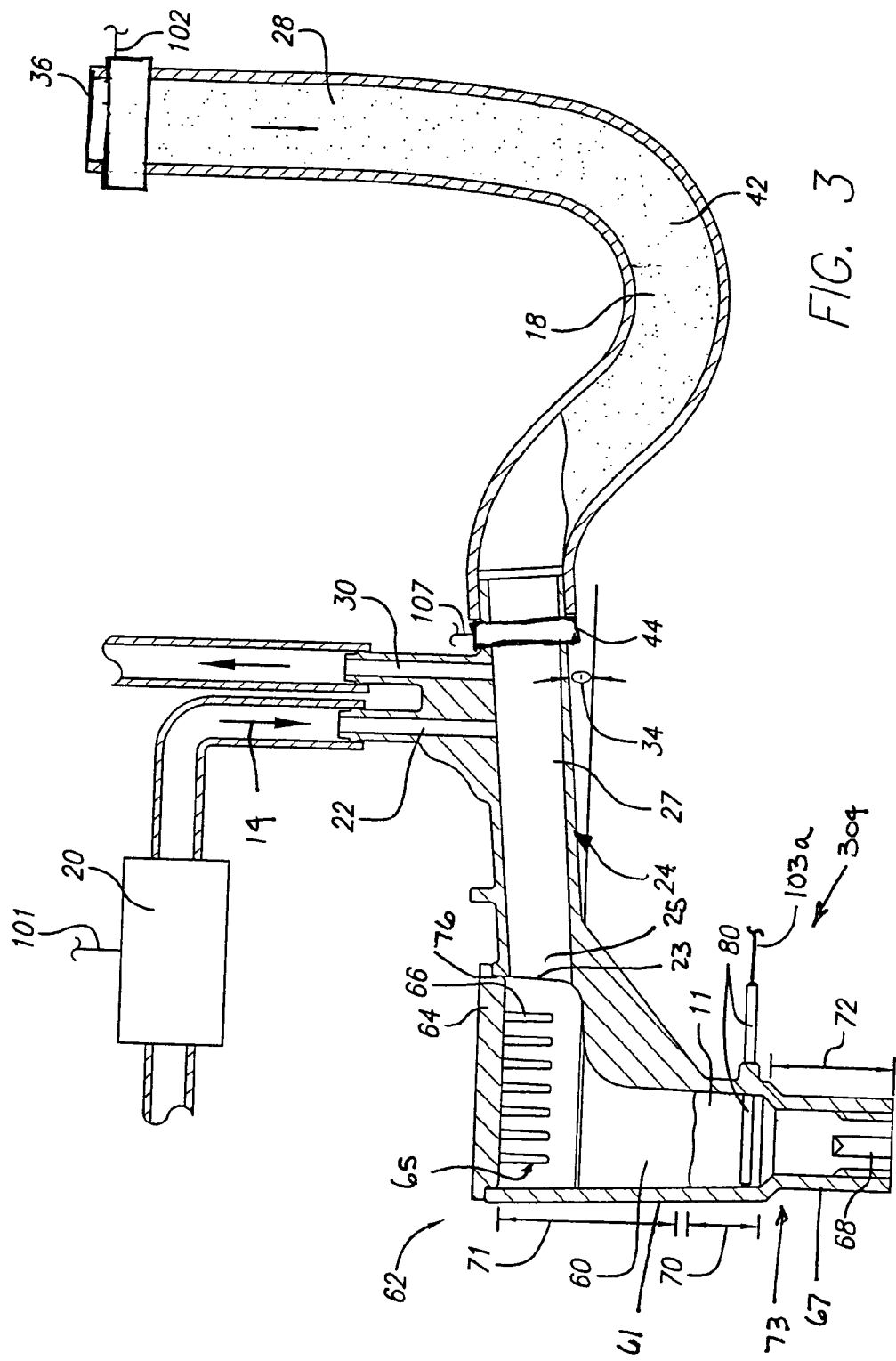
FIG. 3 is an enlarged side elevational view of the serving spout of the beverage dispensing system taken along line 3—3 in FIG. 1.

With reference to FIG. 3, beverage concentrate 14 and diluting water 18 first come into contact with one another at an upper portion 27 of inlet tube 24, where concentrate tube 22 is connected to inlet tube 24. As beverage concentrate 14 and diluting water 18 begin to mix with one another in the upper portion 27 of inlet tube 24 they both continue to flow downstream 25 towards the termination of inlet tube 24 at serving spout assembly 62. This downstream 25 flow of beverage concentrate 14 and diluting water 18 facilitate initial mixing of the two substances by allowing both the beverage concentrate 14 and diluting water 18 to remain in contact with one another for a period of time while they travel towards a terminal end 23 of inlet tube 24. Further mixing is accomplished by natural friction between the interior walls of inlet tube 24 and the beverage 11 contained therein. This friction generates a natural turbulence in the beverage 11 moving within the inlet tube 24.

The location and orientation of concentrate tube 22 along inlet tube 24 also contributes to initial mixing of beverage concentrate 14 and diluting water 18 in the upper portion 27 of inlet tube 24. Concentrate tube 22 is a generally vertical tube, which engages inlet tube 24 proximate to serving spout assembly 62. Concentrate tube 22 engages an upper portion of inlet tube 24 such that any beverage concentrate 14 that flows from concentrate tube 22 into inlet tube 24 may be at least partially assisted by gravity.

This location and orientation assists in the mixing of beverage concentrate 14 and diluting water 18 by allowing diluting water 18 traveling downstream 25 past concentrate tube 22 to come into contact with any volume of beverage concentrate which may be present where concentrate tube 22 and inlet tube 24 are engaged. Because of the downstream 25 flow of diluting water 18, a certain volume of diluting water 18 will be present at the engagement point of inlet tube 24 and concentrate tube 22 for only a small time interval before being replaced by a different volume of diluting water 18. As a result, any beverage concentrate 14 that is introduced into inlet tube 24 at a given time will mix with only the small volume of diluting water 18 present during that time interval, thus allowing a more uniform mixing of the beverage concentrate 14 and diluting water 18.

An additional advantage of the location and orientation of the concentrate tube 22 is preventing solidified or partially solidified beverage concentrate 14 from occluding an opening between the concentrate tube 22 and the inlet tube 24. After a beverage 11 is produced, a small amount of beverage concentrate 14 may remain near the opening between the concentrate tube 22 and the inlet tube 24. Over a period of time exposed to air, this remaining beverage concentrate 14 may partially solidify or "dry" to form a skin occluding the opening between the concentrate tube 22 and the inlet tube 24. When another beverage 11 is produced, the downstream 25 flow of diluting water 18 past concentrate tube 22 will dilute, dislodge, liquefy or dissolve any partially solidified beverage concentrate 14 skin which may have formed.

The downstream 25 flow of fluid within inlet tube 24 towards serving spout 62 is promoted by angle theta 34. As shown in FIG. 3, inlet tube 24 is mounted or otherwise retained within housing 12 in such orientation that angle theta 34 is formed as an acute angle from a horizontal plane. Angle theta 34 causes or otherwise promotes fluid within inlet tube 24 to run from flow restrictor 44 towards serving spout 62 by gravity. The angle 34 also promote draining or drip out of any liquid in the tube 24 and into the serving spout 62 to help clear liquid and prevent accumulation of liquid or concentrate therein.

To prevent backflow of the diluting water 18 and beverage concentrate 14 contained within inlet tube 24, a P-trap 42 is provided. In addition to preventing backflow, the P-trap 42 also improves the overall sanitation of the beverage dispensing system 10.

Proximate to concentrate tube 22 is vent tube 30. Vent tube 30 is connected to inlet tube 24 and provides a form of pressure regulation between the interior of inlet tube 24 and the atmosphere. Pressure regulation provided by vent tube 30 facilitates mixing of beverage concentrate 14 with diluting water 18 by causing additional turbulence within the inlet tube 24 while diluting water 18 flows past concentrate tube 22. An additional benefit of vent tube 30 is that the presence of air bubbles are reduced in the diluting water 18. This occurs because any air bubbles contained within inlet tube 24 may escape to the environment out vent tube 30 as diluting water 18 carries them downstream past vent tube 30.

Vent tube 30 further provides for a release of a vacuum which may occur within the interior of inlet tube 24 when controllable valve 36 is in the closed position. The ability to release a vacuum from the interior of inlet tube 24 allows beverage 11 to drain from the beverage dispensing system 10. Vent tube 30 may terminate at a surface of housing 12 under a cover 32. Cover 32 allows for air exchange between the atmosphere and the interior of vent tube 30 while at least partially covering the terminal portion of outlet tube 30 so as to keep the liquid passing though vent tube 24 free of external debris and sanitary. The vent tube 30 may terminate inside the housing 12 as well. Generally, the housing 12 should not form an airtight seal if the vent tube 30 terminates within the housing 12 so as to allow the vent tube 30 to equalize to ambient pressure.

Figure 2:
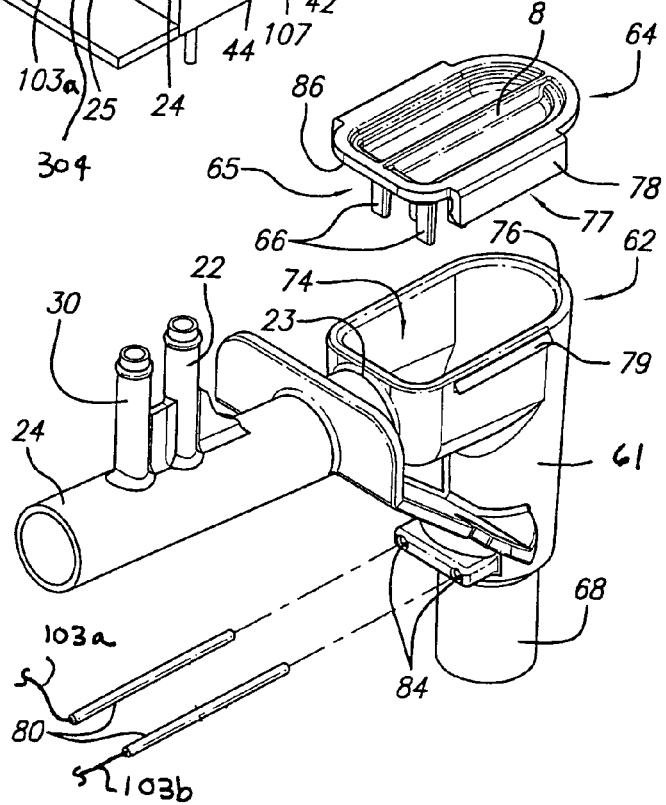
FIG. 2 is an enlarged perspective view of a portion of the beverage dispensing system of FIG. 1 showing a serving spout, supply lines and a pair of conductivity detecting probes.

While the downstream 25 flow, vent-tube 30 and the positioning of concentrate tube 22 facilitate initial mixing of the beverage concentrate 14 and the diluting water 18, additional mixing occurs within the serving spout assembly 62. As seen in FIGS. 2 and 3, serving spout assembly 62 is an outlet from where a user obtains a beverage 11. The serving spout assembly 62 includes a mixing assembly in the form of a mixing chamber 60, a removable cover 64 containing a plurality of protrusions 66 and a laminating structure 68 for producing a generally even columnar flow of beverage 11 from the serving spout assembly 62.

When a beverage 11 is dispensed without being thoroughly mixed, the beverage 11 emerging from a beverage dispensing system 10 may not be of uniform consistency or color. For example, with liquid coffee concentrate an improperly mixed beverage 11 may emerge in patches of dark color and clear water. This lack of uniformity is known as a zebra effect.

Both the flavor characteristics and the visual image are diminished in a beverage 11 displaying a zebra effect. Therefore, it is desirable to ensure that a beverage 11 produced by a beverage dispensing system 10 is thoroughly mixed. To accomplish this goal, the mixing chamber 60 of the present disclosure provides a mixing structure that ensures a beverage 11 is thoroughly mixed before being dispensed from beverage dispensing system 10.

An upper portion 71 of the mixing chamber 60 is generally defined by or otherwise limited by the removable cover 64 while a lower portion 70 of the mixing chamber 60 is defined by or otherwise limited by a flow control portion 73 which is defined by a decrease in diameter or size of the mixing chamber 60. This decreased diameter or size results in an area of decreased diameter 72 which restricts or otherwise controls the flow of beverage 11 out of the mixing chamber 60. As a consequence, beverage 11 generally will tend to pool in the lower portion 70 of mixing chamber 60 just above the flow control portion 73 of decreased diameter 72 and tend to form a small collection or pool of beverage 11.

Turning to the removable cover 64, FIG. 2 shows a structure having an exterior surface 85 and an interior surface 86 which is dimensioned to cover an aperture 74 defining a top edge 63 of serving spout assembly 62. The aperture 74 of serving spout assembly 62 is defined by a perimeter 76. Perimeter 76 is the uppermost area of the serving spout assembly 62 which engages removable cover 64.

In one embodiment, removable cover 64 is a rubberized or elastomeric structure dimensioned to cover aperture 74. Means 78 for removably fastening the cover on the body are provided on the removable cover 64 and body. The fastening means facilitates removable engagement of the cover on the body. One form of such fastening means 78 is shown as a flexible flange or flexible rail 77 which articulates with a corresponding protrusion or rib 79 on serving spout assembly 62 to allow for removable engagement of removable cover 64 and serving spout assembly 62.

The removable cover 64 allows a user easy access to an interior of mixing chamber 60. Access to the interior of mixing chamber 60 is desirable for greater sanitation. In order to sanitize the mixing chamber 60 in prior beverage dispensing systems 10, it was necessary to flush the serving spout assembly 62 with water from the beverage dispensing system 10. Even after flushing, periodic thorough sanitation procedures may be required. In the present disclosure however, it is easy to manually clean and inspect the interior of mixing chamber 60 by simply removing removable cover 64. The cover 64 can be easily separated from the mixing chamber 60 and placed in an automatic sanitizer of dish washing machine.

Extending from an interior surface 86 of removable cover 64 are means for mixing 65. One form of such mixing means 65 is a plurality of protrusions 66, dimensioned to protrude into the area adjacent to a terminal end 23 of inlet tube 24. Terminal end 23 of inlet tube 24 is connected to serving spout assembly 62 proximate to perimeter 76 of serving spout assembly 62. It is contemplated that protrusions 66 may extend at least partially into the path of a beverage 11 flowing from inlet tube 24 so as to disrupt the flow of beverage 11 out of inlet tube 24. The protrusions 66 may also extend the entire diameter of inlet tube 24. As shown, the protrusions are a plurality of spaced part extending fingers generally axially aligned and extending into the flow path for agitating the flow as it passes from the inlet tube to the chamber.

The mixing means 65 are not limited to the embodiment of the protrusions 66 as illustrated and may take any form and arrangement suitable for disrupting a flow of beverage 11 from the inlet tube 24. In one embodiment, the protrusions 66 are formed in pairs and are oriented in offset rows extending along a longitudinal axis of the interior surface 86 of removable cover 64. Other variations and orientations of protrusions 66 such as a diagonal orientation formed in offset rows may be used. It is contemplated that those of skill in the art may use other variations and orientations of protrusions which accomplish the same function.

The mixing means 65, in any form cause the flow path of the beverage 11 flowing from inlet tube 24 to be disrupted. By disrupting the flow path, the mixing means 65 enhance the combination of beverage concentrate 14 and diluting water 18 to more thoroughly mix with one another. The mixing is accomplished by allowing a portion of the beverage 11 to flow partially through the protrusions 66 thereby agitating the flow and delaying the downward flow of a portion of the beverage 11, in effect blending the beverage concentrate 14 and diluting water 18. At the same time, another portion of the beverage 11 is disrupted by the protrusions 66 and is more rapidly directed downward into a pool of beverage 11 in the lower portion 70.

The lower portion 70 of mixing chamber 60 is designed with a decreased diameter or size and thus restricts the flow of beverage 11 from mixing chamber 60. The result of the decreased diameter or size is that beverage 11 backs up and pools in the lower portion 70. The restricted flow caused by the decreased diameter causes beverage 11 to accumulate or pool. When a beverage 11 pools in the lower portion 70, it does so only momentarily before flowing out of mixing chamber 60 and into laminating structure 68. The volume of beverage 11 that pools in the lower portion 70 of mixing chamber 60 is minimal.

Although only a minimal volume of beverage 11 pools in lower portion 70, the pooling contributes to overall mixing of beverage concentrate 14 with diluting water 18. After a beverage 11 flows from the inlet tube 24 downward into the pool of beverage 11 in the lower portion 70, the beverage 11 which most recently enters the pool of beverage 11 will naturally agitate and mix with the volume of beverage 11 pooling in the lower portion 70. The agitation and mixing of beverage 11 within the pool of beverage 11 further enhances mixing of the overall beverage 11 prior to dispensing.

The laminating structure 68 is located below the lower portion 70 of mixing chamber 60 within the nozzle 67 of decreased diameter 72 and is the last structure the beverage 11 comes into contact with prior to being dispensed. The laminating structure 68 is positioned within the lowermost portion of the serving spout assembly 62.

The laminating structure 68 may take a variety of forms known to those of skill in the art. In one embodiment as shown in FIG. 3, the laminating structure 68 is an elongated structure having vertical ribs, centrally formed within the area of decreased diameter or size 72 of the serving spout assembly 62. In this position, the laminating structure 68 facilitates an even flow of beverage 11 from serving spout assembly 62 by directing the beverage 11 downward and encouraging the flow of beverage 11 to orient more centrally where serving spout assembly 62 terminates. The more centrally oriented flow of beverage 11 creates a generally columnar form of beverage 11 by preventing the flow from becoming diffuse which reduces undesired splashing or splattering of the beverage 11. The vertical ribs of the laminating structure 68 also help to prevent beverage 11 from forming a bubble at the terminal end of the serving spout assembly 62 and thus reduce splashing of the beverage 11 as it flows from serving spout assembly 62.

An additional advantage the laminating structure 68 provides is an another disruption of the flow of beverage 11. This flow disruption creates some level of turbulence in beverage 11 thus providing additional mixing of the beverage 11 before it flows from serving spout assembly 62.

Turning now to the control aspects of the present disclosure, beverages 11 dispensed by the beverage dispensing system 10 can be characterized by a desired flavor range, flavor profile, or other defining characteristics. The flavor range for each beverage 11 is expressed in the present system 10 in the controller 100 as a conductivity measurement. Each beverage 11 dispensed by the beverage dispensing system 10 is defined in terms of a conductivity measurement which is stored in the controller 100. It is also contemplated that a plurality of conductivity measurements may be input into the controller 100 for the same type of beverage. For example with coffee, a strong flavor and a mild flavor may be input into the controller 100 as two distinct conductivity measurements. The beverage dispensing system 10 may then be preprogrammed to dispense coffee with one of the two possible flavors from the same beverage concentrate 14. Further, the flavor may be selectable by a user from the control panel 50. The control panel 50 is generally of known construction and is coupled to the controller 100 over line 208.

As seen in FIG. 3, two conductivity probes 80 are provided in the lower portion 70 of the interior of mixing chamber 60. The conductivity probes 80 are positioned in the lower portion 70 because the mixing chamber 60 is designed with a decreased diameter or size to cause a pooling of beverage 11 in the lower portion 70. When a beverage 11 pools in the lower portion 70, the beverage 11 in the pool may be measured by the conductivity probes 80 more accurately than a beverage which only comes into contact with the conductivity probes 80 momentarily as it flows past. The pooling also causes the probes 80 to be fully immersed in and surrounded by mixed beverage to provide a more accurate reading. This pooling of beverage 11 also ensures that more accurate readings are possible by conductivity probes 80 by reducing the probability that air bubbles may form proximate to the conductivity probes 80 and interfere with or create inaccurate readings. Therefore, placing the conductivity probes 80 in a location where a beverage 11 pools will yield a more accurate reading of the conductivity of the beverage 11 being produced by beverage dispensing system 10.

Figure 4:
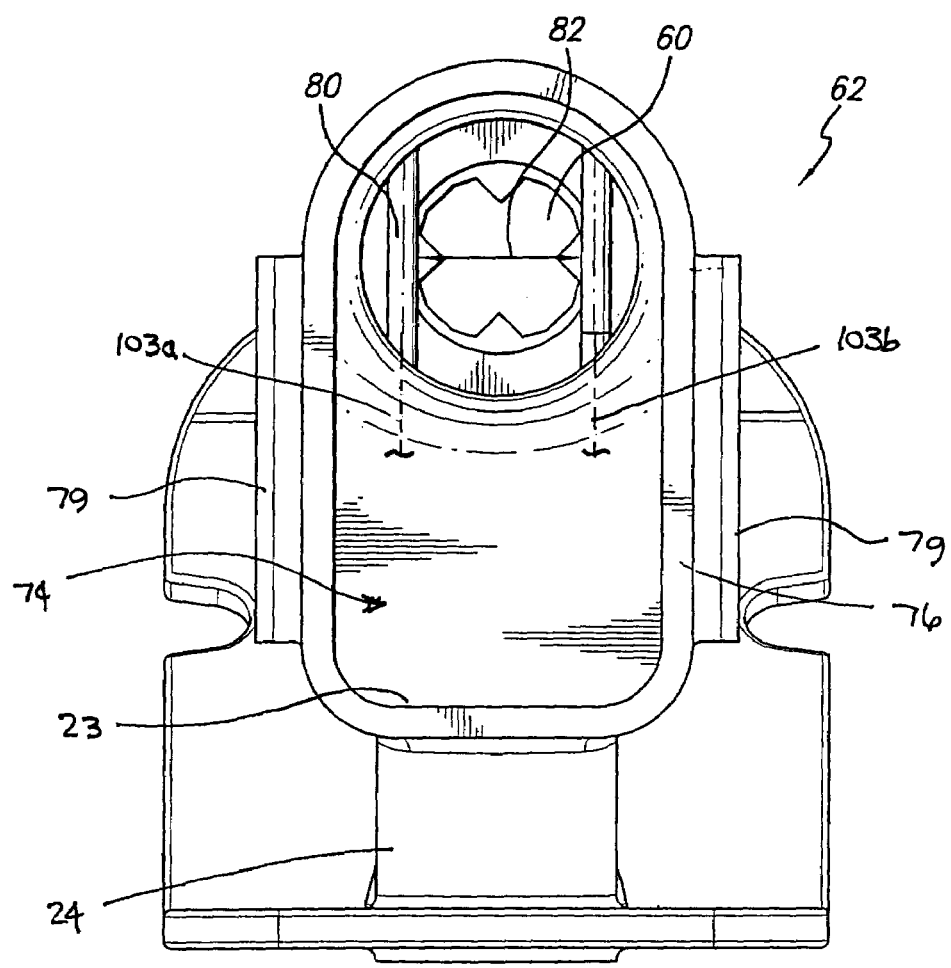
FIG. 4 is a plan view from above an outlet aperture of the serving spout and from which a cover has been removed showing the pair of conductivity probes.

A variety of orientations of the conductivity probes 80 are contemplated by the present disclosure. As shown in FIG. 4, one embodiment contemplates that the conductivity probes 80 are oriented in generally parallel alignment with each other in substantially the same plane and are spaced apart by a predetermined distance 82. The probes are oriented longitudinally across a diameter of the mixing chamber 60 in a generally horizontal plane to make available a greater surface area for a beverage 11 to contact. In one embodiment, the conductivity probes 80 are inserted through apertures 84 in the mixing chamber 60. In one embodiment, the probes are press fit into the apertures. The press fit is achieved by sizing the apertures 84 to be slightly smaller than the corresponding dimension of the probes 80. When the body 61 of the spout 62 is formed of a plastic material and the probe is formed of a material which generally is harder than the material used to form the body 61. Insertion of the probes into the apertures 84 will tend to force the probe 80 into the material providing a tight fit between the probes and apertures 84. The tight fit prevents leakage of liquid through the apertures 84 along the probe 80.

It is also contemplated that other orientations and numbers of the conductivity probes 80 may be used. For example, conductivity probes 80 may be integrally molded or "in-molded" into the sides of the mixing chamber 61. In this orientation, the conductivity probes 80 will form two discrete portions of the interior surface of the mixing chamber 60. These discrete portions may lie within the same plane or in a non-planar orientation.

In another orientation, conductivity probes 80 may be inserted through apertures 84 in the mixing chamber 60 and terminate at the inner surface of the mixing chamber 60, exposing only a terminal end of the conductivity probe 80. These conductivity probes 80 may be disposed on opposite sides of the mixing chamber 60, proximate to one another, in a different planar orientation, vertically oriented, angularly oriented, or in any other orientation which those of skill in the art may find practical. In any orientation, conductivity probes 80 are provided in the interior of the mixing chamber 60 for measuring the conductivity of a beverage 11 which pools therein. It is also contemplated that photometric sensors may be used instead of conductivity probes 80 to detect the relative amount of beverage concentrate 14 within a beverage 11 in the mixing chamber 60. The components including the probes 80 connected to the controller 100 and lines 103a, 103b comprise one form of means for detecting conductivity 304 or a conductivity detector.

The conductivity probes 80 are coupled over a line 103 to controller 100. The conductivity probes 80 are electrodes which are spaced apart a predetermined distance. The conductivity probes 80 are electrically insulated from one another in their attachment to the body 61 through the use of an insulating material or insulating jacket on the probes so as to allow the conductivity probes 80 to accurately measure without interference from the material forming the mixing chamber 60. The probes 80 are conductive within the chamber 60 with the liquid in the chamber 60 forming a path conductively coupling the probes 80 in the chamber 60. The conductivity probes 80 provide measurements of the electrical conductivity of the beverage 11 contained in an area in which the probes lie, generally between the conductivity probes 80. The measurements are taken at preprogrammed time intervals throughout the time period a beverage 11 is being dispensed, thus allowing real time feedback to the controller 100.

The measurements are taken by passing a known electrical current through 103a, coupled to the controller 100, a first of two conductivity probes 80 into a beverage 11 contained within the lower portion 70 of mixing chamber 60. The electrical current received at a second conductivity probe 80 is detected by the controller 100, over line 103b, and measured to derive a conductivity measurement of the beverage 11. The measurement of electrical current that is detected by the second conductivity probe 80 is communicated over line 103b to controller 100 in real time as the beverage concentrate 14 and diluting water 18 are dispensed through inlet tube 24 into the mixing chamber 60.

Controller 100 interprets the real time conductivity measurements by comparing them against a preprogrammed or user selected target conductivity reading or range of readings. If the real time conductivity measurements of the conductivity probes 80 fall within the preprogrammed range of conductivity readings, the beverage being produced is deemed to be within the desired range and the controller 100 will continue to operate the pump 20 at its current speed or otherwise deliver concentrate at a desired rate.

If the real time conductivity measurements are outside of the preprogrammed range of conductivity readings, the beverage 11 being produced is deemed to be outside the desired range. In this case, the controller 100 will either increase or decrease the rate of pump 20 dependant on whether the real time conductivity measurements fall below or above the preprogrammed range of conductivity readings.

As the speed of pump 20 is adjusted by controller 100, the volume of beverage concentrate 14 is either increased or decreased to bring the subsequent real time conductivity measurements within the preprogrammed range of conductivity readings. The resulting beverage that enters the mixing chamber 60 is then measured by the conductivity probes 80 and communicated to controller 100 which again compares the real time conductivity measurements to the preprogrammed range of conductivity readings and either maintains the speed of pump 20 or adjusts the speed again to bring the real time conductivity measurements within the preprogrammed range of conductivity readings.

While it is contemplated that the controller may adjust both the speed of pump 20 and the relative position of controllable valve 36 and flow restrictor 44, in one embodiment the pump 20 is an example of the primary means for controlling the concentration of beverage concentrate 14 in the beverage 11, and thus the conductivity. In one embodiment, the pump 20 is a peristaltic pump. The controller 100 can slightly increase or decrease the speed of a peristaltic pump based on readings of the conductivity probes 80 in order to precisely increase or decrease the volume of beverage concentrate 14 being dispensed. While a peristaltic pump is disclosed, other pumps and means for controllably delivering concentrate are contemplated which will serve the same function.

By interpreting and responding to changes in the real time conductivity data being gathered by the conductivity probes 80, the controller 100 can adapt to any fluctuations in the conductivity of the beverage 11 being dispensed and ensure that the beverage 11 being dispensed is more uniform and falls within a more precise range.

An additional feature which the present disclosure provides is the ability to monitor when the container 16 has generally exhausted the supply of beverage concentrate 14. The conductivity probes 80 may detect a change in conductivity of the beverage 11 produced after appropriate adjustments in pump 20 speed have been made. Such measurements may then be communicated to controller 100 over line 103. The controller 100 may respond to the conductivity measurements if they are outside a preprogrammed range by locking out the beverage dispensing system or indicating that the container 16 is empty on the control panel 50. For example, if the conductivity probes 80 detect a decrease or increase in conductivity of greater than 50%, the controller may be preprogrammed to lockout the beverage dispensing system 10 and indicate that the container 16 holding beverage concentrate 14 is empty.

An additional feature which the present disclosure provides is the ability to monitor when the container 16 has generally exhausted the supply of beverage concentrate 14. The conductivity probes 80 may detect a change in conductivity of the beverage 11 produced after appropriate adjustments in pump 20 speed have been made. Such measurements may then be communicated to controller 100 over line 103. The controller 100 may respond to the conductivity measurements if they are outside a preprogrammed range by locking out the beverage dispensing system or indicating that the container 16 is empty on the control panel 50. For example, if the conductivity probes 80 detect a decrease or increase in conductivity of greater than 50%, the controller may be preprogrammed to lockout the beverage dispensing system 10 and indicate that the container 16 holding beverage concentrate 14 is empty.

While preferred embodiments have been illustrated and described in detail in the drawings and foregoing description, such illustrations and descriptions are considered to be exemplary and not restrictive in character, it being understood that only illustrative embodiments have been shown and described and that all changes and modifications that come within the spirit of the invention are desired to be protected. There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods that incorporate one or more of the features of the disclosure and fall within the spirit and scope of the present disclosure as defined by the appended claims.

The invention claimed is:

1. A mixing assembly for use with a beverage dispenser to combine a concentrate and a dilution material to make a beverage, the mixing assembly comprising:
   a body defining a generally hollow chamber;
   an inlet tube defining a passage and communicating with the chamber;
   a cover extending over a portion of the chamber; and at least one protrusion extending from the cover inwardly towards the chamber and extending at least partially into a path defined by the passage of the inlet tube, the at least one protrusion contacting a flow of dilution material and concentrate passing through the inlet tube into the chamber.

2. The mixing assembly of claim 1 further comprising, the cover being removably attached to the body.

3. The mixing assembly of claim 1 further comprising, the at least one protrusion comprising a plurality of spaced part extending fingers generally axially aligned and extending into a flow path for agitating the flow as it passes from the inlet tube to the chamber.

4. The mixing assembly of claim 1 further comprising the body defining an upper chamber and a generally reduced dimension lower chamber, the reduced dimension lower chamber causing pooling of the beverage in the chamber.

5. The mixing assembly of claim 1 further comprising a conductivity detector for detecting conductivity of beverage in the chamber.

6. The mixing assembly of claim 5 further comprising the conductivity detector including at least a pair of spaced apart conductivity probes, the probes being spaced apart in the chamber for detecting conductivity of material flowing through the chamber.

7. The mixing assembly of claim 6 further comprising the conductivity probes being generally elongated and extending generally parallel to one another in the chamber.

8. The mixing assembly of claim 6 further comprising the conductivity probes generally oriented in a common plane.

9. The mixing assembly of claim 5 further comprising the conductivity detector including a pair of spaced apart probes, the probes being generally oriented parallel to one another and lying in a common plane.

10. The mixing assembly of claim 2 further comprising the cover being formed of an elastomeric material.

11. The mixing assembly of claim 2 further comprising means for removably fastening the cover to the body, the fastening means facilitating removable engagement of the cover on the body.

12. The mixing assembly of claim 11 the fastening means further comprising a flexible flange on the cover for engaging a protrusion on the body, the flexible flange and protrusion being engageable for retaining the cover on the body.

13. A beverage producing apparatus having mixing assembly for combining a concentrate and a dilution material to produce a beverage, the beverage producing apparatus comprising:
 a controllable concentrate dispensing assembly;
 a controllable dilution material dispensing assembly;
 a controller operatively coupled to and operatively controlling the concentrate dispensing assembly and the dilution material dispensing assembly;
 a body defining a generally hollow chamber of the mixing assembly;
 an inlet tube defining a passage and communicating with the chamber;
 a cover extending over a portion of the chamber;
 at least one protrusion extending from the cover inwardly towards the chamber and extending at least partially into a path defined by the passage of the inlet tube, the at least one protrusion contacting a flow of dilution material and concentrate passing through the inlet tube into the chamber; and
 a conductivity detector, the conductivity detector being operatively coupled to the controller for providing conductivity information relating mixing of concentrate and dilution material in the mixing assembly, the controller operatively controlling the dispensing of concentrate and dilution material to maintain the conductivity of the mixture within at least one of a predetermined conductivity level and a predetermined conductivity range.

14. The beverage producing apparatus of claim 13 further comprising the cover being removably attached to the body.

15. The beverage producing apparatus of claim 13 further comprising the at least one protrusion comprising a plurality of spaced part extending fingers generally axially aligned and extending into a flow path for agitating the flow as it passes from the inlet tube to the chamber.

16. The beverage producing apparatus of claim 13 further comprising the body defining an upper chamber and a generally reduced dimension lower chamber, the reduced dimension lower chamber causing pooling of the beverage in the chamber.

17. The beverage producing apparatus of claim 13 further comprising the conductivity detector including at least a pair of spaced apart conductivity probes, the probes being spaced apart in the chamber for detecting conductivity of beverage flowing through the chamber.

18. The beverage producing apparatus of claim 17 further comprising the conductivity probes being generally elongated and extending generally parallel to one another in the chamber.

19. The beverage producing apparatus of claim 18 further comprising the conductivity probes generally oriented in a common plane.

20. The beverage producing apparatus of claim 13 further comprising the conductivity detector including a pair of spaced apart probes, the probes being generally oriented parallel to one another and lying in a common plane.

21. The beverage producing apparatus of claim 13 further comprising the cover being formed of an elastomeric material.

22. The beverage producing apparatus of claim 13 further comprising means for removably fastening the cover to the body, the fastening means facilitating removable engagement of the cover on the body.

23. The beverage producing apparatus of claim 22 further comprising the fastening means further comprising a flexible flange on the cover for engaging a protrusion on the body, the flexible flange and protrusion being engageable for retaining the cover on the body.

24. A mixing assembly for use with a beverage dispenser to combine a concentrate and a dilution material to make a beverage, the mixing assembly comprising:
 a body defining a generally hollow chamber;
 an inlet tube defining a passage and communicating with the chamber;
 a cover extending over a portion of the chamber; and
 a plurality of spaced part extending protrusions generally extending from the cover inwardly towards a flow path from the passage to the chamber for agitating the flow as it passes from the inlet tube to the chamber.

25. The mixing assembly of claim 24 further comprising the protrusions being generally axially aligned and extending into the flow path.

26. The mixing assembly of claim 24 further comprising a conductivity detector for detecting conductivity of beverage in the chamber, the body defining an upper chamber and a generally reduced dimension lower chamber, the reduced dimension lower chamber causing pooling of the beverage in the chamber, at least a portion of the conductivity detector extending into the lower chamber for detecting the conductivity of the beverage pooled in the lower chamber.

27. The mixing assembly of claim 26 further comprising the conductivity detector including at least a pair of spaced apart conductivity probes, the probes being spaced apart in the chamber for detecting conductivity of the beverage pooled in the lower chamber.

28. The mixing assembly of claim 27 further comprising the conductivity probes being generally elongated and extending generally parallel to one another in the lower chamber.

29. The mixing assembly of claim 27 further comprising the conductivity probes generally oriented in a common plane.

30. The mixing assembly of claim 26 further comprising the conductivity detector including a pair of spaced apart probes, the probes being generally oriented parallel to one another and lying in a common plane.

31. The mixing assembly of claim 24 further comprising the cover being formed of an elastomeric material.

32. The mixing assembly of claim 24 further comprising means for removably fastening the cover to the body, the fastening means facilitating removable engagement of the cover on the body.

33. The mixing assembly of claim 32 the fastening means further comprising a flexible flange on the cover for engaging a protrusion on the body, the flexible flange and protrusion being engageable for retaining the cover on the body.

* * * * *